(12) United States Patent
Peyton et al.

(10) Patent No.: US 7,569,146 B2
(45) Date of Patent: *Aug. 4, 2009

(54) BY-PRODUCTS FROM FERMENTATION STILL BOTTOMS

(75) Inventors: Thomas O. Peyton, Lafayette, IN (US); Birgitte Kiaer Ahring, Hoersholm (DK); Lars Erik Rohold, Odense (DK)

(73) Assignee: NouvEau Inc., LaFayette, IN (US)

( * ) Notice: Subject to any disclaimer, the term of this patent is extended or adjusted under 35 U.S.C. 154(b) by 151 days.

This patent is subject to a terminal disclaimer.

(21) Appl. No.: 11/796,536

(22) Filed: Apr. 27, 2007

(65) Prior Publication Data

US 2007/0199894 A1    Aug. 30, 2007

Related U.S. Application Data

(63) Continuation-in-part of application No. 11/127,670, filed on May 12, 2005, now Pat. No. 7,267,774.

(51) Int. Cl.
C02F 3/28 (2006.01)
B01D 61/00 (2006.01)

(52) U.S. Cl. .............. 210/603; 210/641; 210/650; 210/652; 203/DIG. 25; 426/66

(58) Field of Classification Search ........... 210/603, 210/641, 649, 650, 652, 353, 359; 203/DIG. 25; 426/66

See application file for complete search history.

(56) References Cited

U.S. PATENT DOCUMENTS

| | | | | | |
|---|---|---|---|---|---|
| 3,040,060 | A | * | 6/1962 | Kulik | ............ 549/250 |
| 3,784,457 | A | * | 1/1974 | Mizutani et al. | ........ 204/529 |
| 4,001,198 | A | * | 1/1977 | Thomas | ............ 530/414 |
| 4,770,786 | A | * | 9/1988 | Manabe et al. | ........ 210/640 |
| 4,812,232 | A | | 3/1989 | Weiss | |
| 4,952,503 | A | * | 8/1990 | Granstedt | ............ 435/161 |
| 4,959,237 | A | * | 9/1990 | Walker | ............ 426/330.5 |
| 4,988,525 | A | | 1/1991 | Gresch | |
| 4,999,209 | A | | 3/1991 | Gnekow | |

(Continued)

OTHER PUBLICATIONS

O'Bryan et al "Developing Enzyme Systems for Converting Pretreated DDGS to Fermentable Sugars" National Center for Agricultural Utilization Research, Peoria, IL Midwest Consortium for Biobased Products & Bioenergy & DOE Grant #DE-FG36-04G014220 off Internet copy attached date unknown.

Primary Examiner—Fred Prince

(57) ABSTRACT

The disclosed invention is an improved method for treating ethanol distillation still bottoms by recovering, through solids separation and pressurized membrane filtration, potable water from still bottoms for human consumption by bottling or for reuse, and concentrating the solids with beneficial properties recovered such as chemicals, nutrients and medicinals before anaerobic digestion. The invention is an improved process because it can reduce the volume of solids to manage, recovers the water from the fermentation still bottoms while pasteurized, maintains the chemical arid physical properties of solids for beneficial property recovery, improves ethanol and energy efficiency, and results in clean discharge to the environment including carbon dioxide recovery. A bioreactor produces a gas rich in methane fuel from the concentrate to power the pressurized tiltration process and an aqueous ammonia solution to recover or recycle. This invention improves environmental quality, conserves energy, and produces a beverage water for bottling that can be of an organic origin with reliable source and quality.

20 Claims, 3 Drawing Sheets

U.S. PATENT DOCUMENTS

| | | | |
|---|---|---|---|
| 5,032,265 A * | 7/1991 | Jha et al. | 210/195.2 |
| 5,177,008 A * | 1/1993 | Kampen | 435/139 |
| 5,250,182 A * | 10/1993 | Bento et al. | 210/641 |
| 5,374,356 A * | 12/1994 | Miller et al. | 210/641 |
| 5,773,526 A * | 6/1998 | Van Dijk et al. | 210/603 |
| 6,008,260 A | 12/1999 | Pezzuto et al. | |
| 6,036,854 A * | 3/2000 | Potter | 210/177 |
| 6,368,849 B1 * | 4/2002 | Norddahl | 210/603 |
| 6,423,236 B1 * | 7/2002 | Shiota et al. | 210/761 |
| 6,861,085 B2 | 3/2005 | Melwitz et al. | |

* cited by examiner

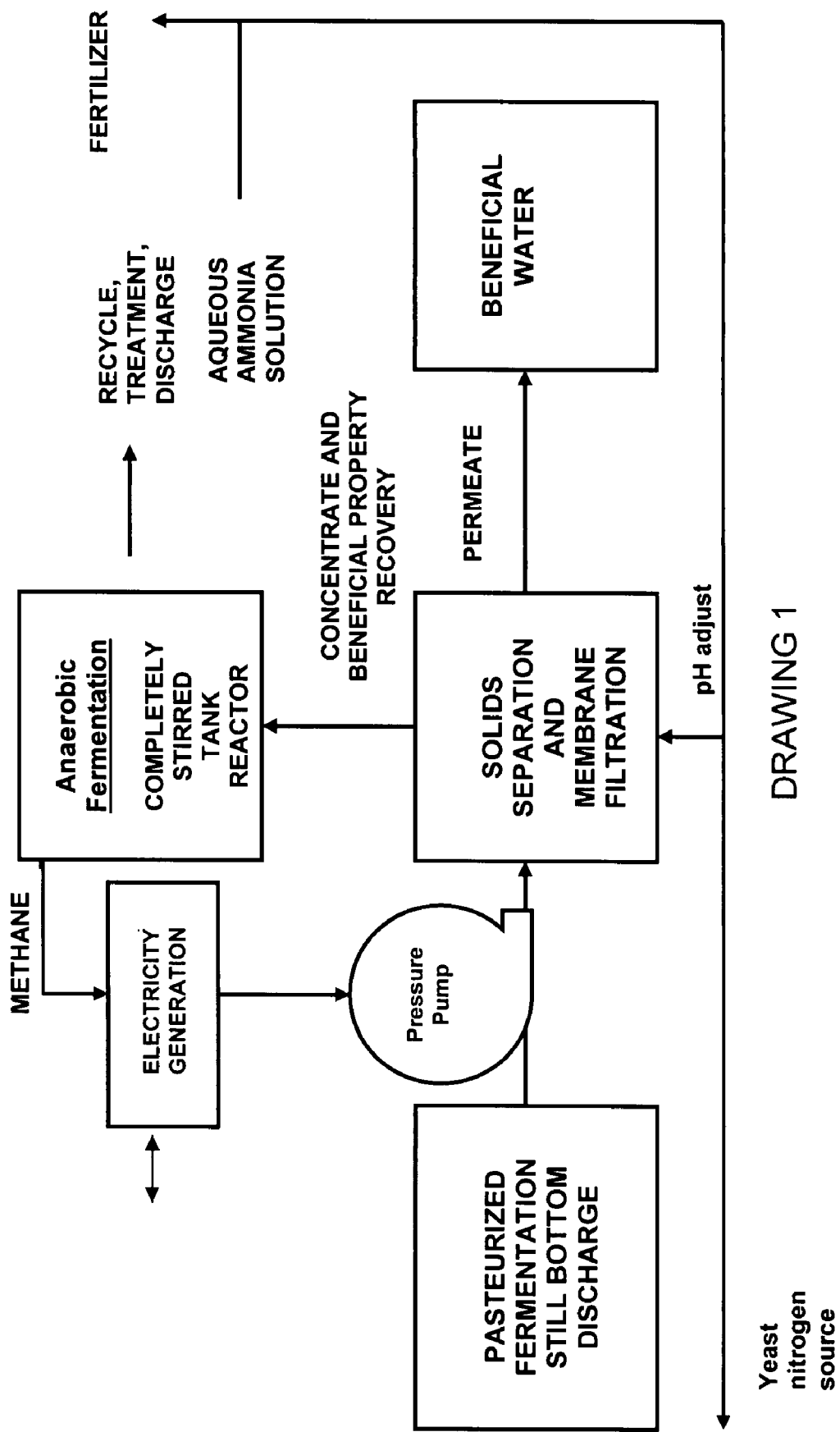
DRAWING 1

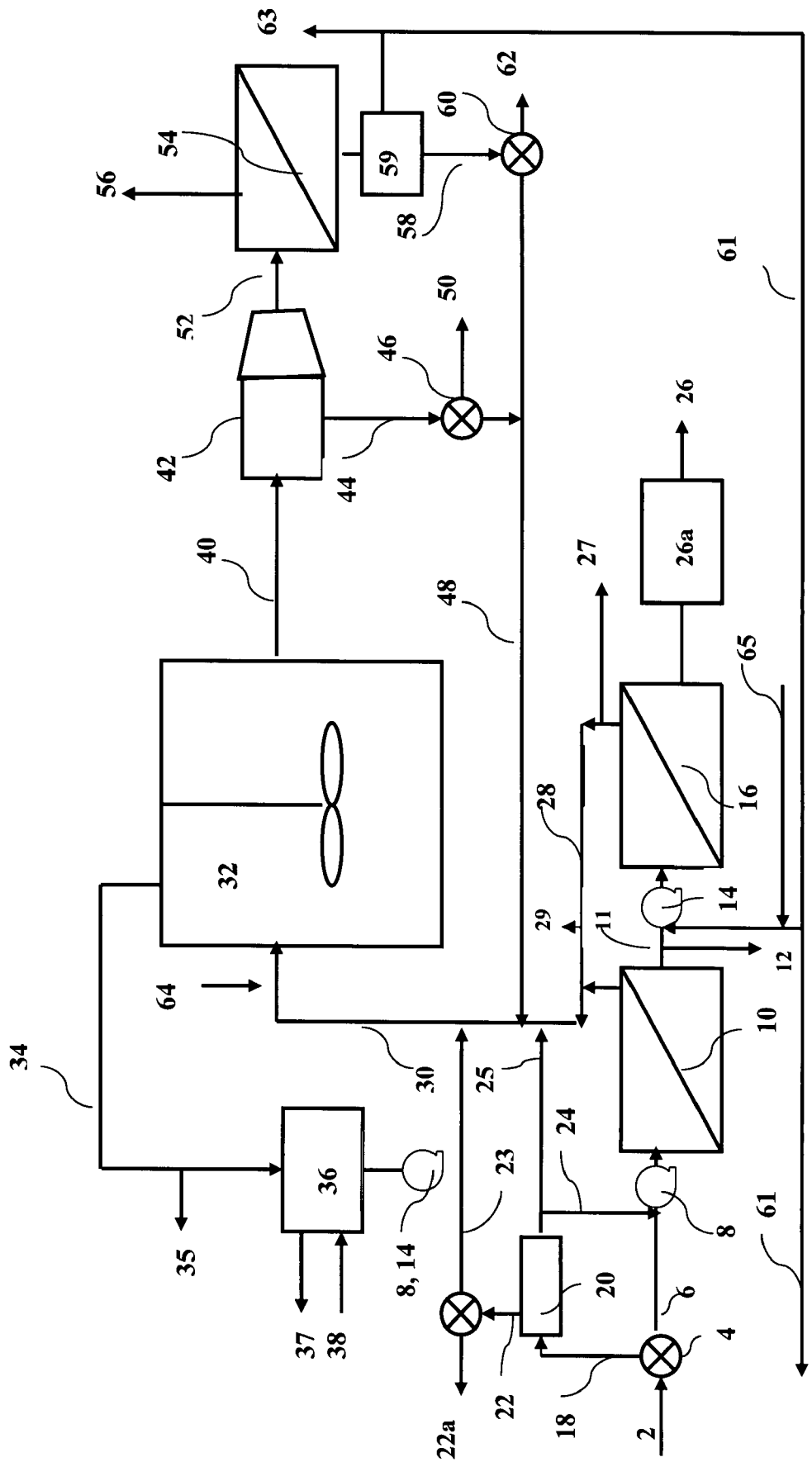
DRAWING 2

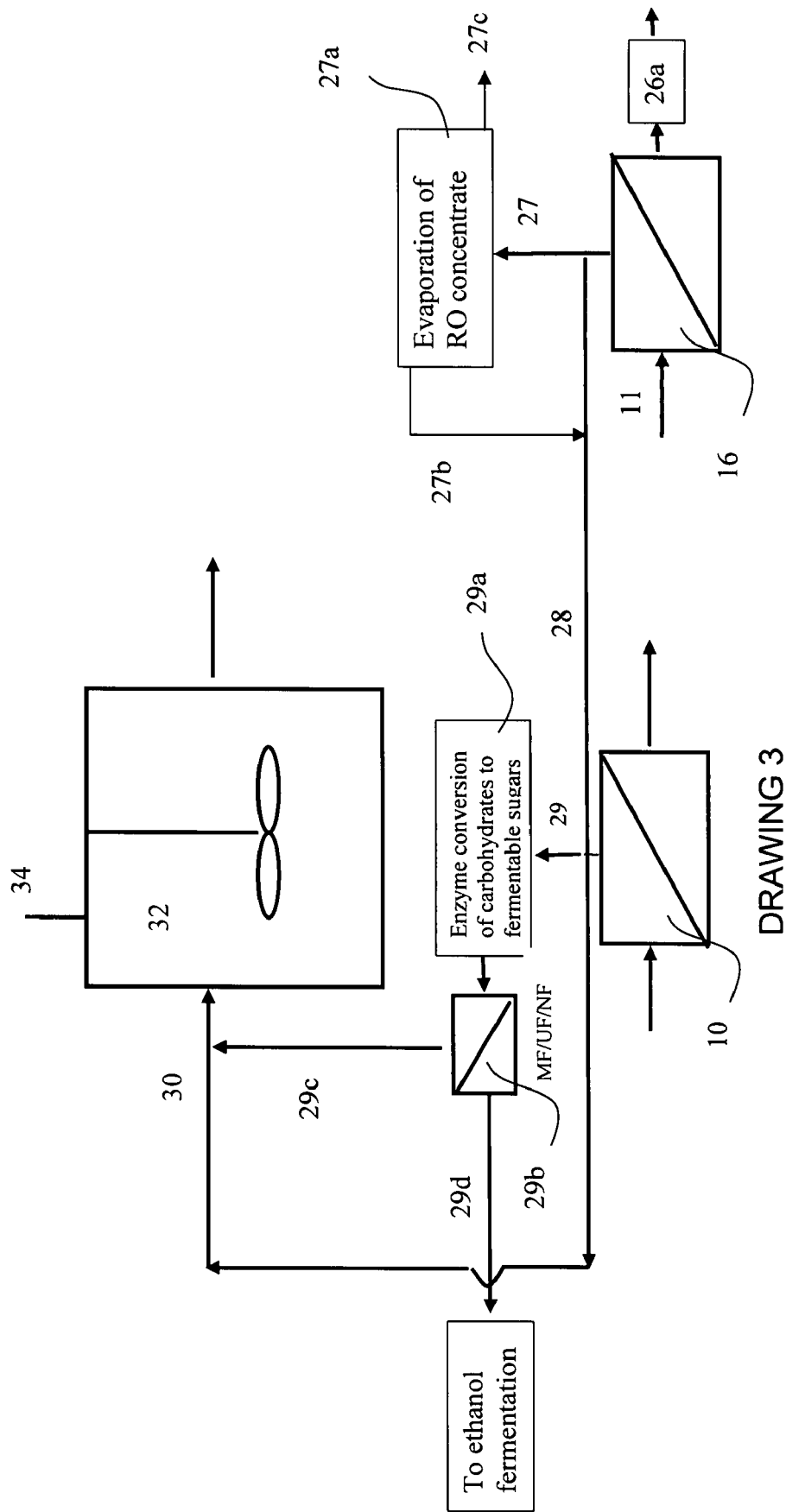

BY-PRODUCTS FROM FERMENTATION STILL BOTTOMS

CROSS-REFERENCE TO RELATED APPLICATIONS

This application is a continuation-in-part of prior application Ser. No. 11/127,670 filed on May 12, 2005 by the present inventors now U.S. Pat. No. 7,267,774.

FEDERALLY SPONSORED RESEARCH

Not Applicable

SEQUENCE OR PROGRAM

Not Applicable

BACKGROUND OF THE INVENTION

1. Field of the Invention

The disclosed invention relates to an improved method for treating ethanol fermentation still bottoms and recovering useful products there from. More specifically, this invention advantageously separates the solid and liquid residues while pasteurized by pressure across membrane filters in sanitary conditions with the permeate retaining low molecular weight minerals and nutrients at low to almost no concentration to make a unique non-alcoholic beverage or clean water for reuse in the process. Further, the means is unique and advantageous for the separated still bottom solids to be simultaneously concentrated for anaerobic digestion to produce fuels at a remote location and to have beneficial properties recovered before anaerobic digestion thereby producing chemicals, nutrients and medicinals.

2. Prior Art

Most of the 4000 alcohol distilleries in the world use starch and sugar feedstock up to 20% concentration in water for ethanol yeast fermentation that is heated to boiling in a column or pot still to evaporate the volatile fermentation products, mostly azeotropic ethanol, that condense in a column separator and the residuals are discharged as hot still bottoms that can contain from 1-10% inorganic and organic dissolved and suspended solids composed mostly of spent yeast cells and cell parts, metabolites, fermentation by-products, and non- fermentable starch and sugar feedstock residues. Distillation can also occur at lesser temperatures and lower pressures as in vacuum distillation. Nitrogen is often added to culture yeast before fermentation and typical yeast is composed of nearly 90% protein and carbohydrates. Following distillation this distilled fermentation water is often discharged directly to a water course, decanted into heavier and lighter fractions, or is evaporated to recover the solids as animal feed, filtered to recover other fermentation by-products from a concentrate, or biologically treated by anaerobic digestion to recover methane fuels. There are no unit methods known or found in the related art where discharged still bottoms are first pressure filtered in their pasteurized state with potable water recovered for human consumption and beneficial properties of the solid concentrate recovered before the remaining solids are sent to a anaerobic bioreactor that recovers methane to power the pressurized membrane filtration in an energy efficient process.

Pressure filtrations are most frequently used in the agricultural and food processing industry to concentrate solid and separate liquid fractions through porous membranes. For example, in U.S. Pat. No. 4,959,237 by Walker, a series of reverse osmosis units are used to concentrate fruit juice to improve the product quality and in U.S. Pat. No. 4,001,198 by Thomas, ultrafiltration is used to concentrate and pasteurize cheese whey nutrients. In Walker's invention, the permeate is recycled back to reverse osmosis and in Thomas' invention the permeate is discharged. In neither case is the permeate used as potable water and pasteurization is required in Thomas' to maintain sanitary condition of the concentrate. In U.S. Pat. No. 5,250,182, Bento et al invent a plurality of membrane based processes following centrifugation including microfiltration, ultrafiltration, nanofiltration and reverse osmosis to recover lactic acid and glycerol from a corn thin stillage stream following industrial ethanol fermentation and distillation that obviates the need for evaporation to concentrate syrup and produce lactic acid-free and glycerol-free animal feed upon drying with a filtration permeate that produces mineral free water to recycle as makeup water to the ethanol fermentation zone or as boiler water make-up. Bento et al's light stillage filtration invention means not to produce methane through anaerobic fermentation of the concentrate for an energy efficient pressurized filtration and means not to produce a nutrient water under sanitary conditions from pasteurized permeate for human consumption. Similarly, in U.S. Pat. No. 5,032,265 Kampen uses centrifugation and microfiltration first to preferentially remove coarse solids from stillage before subjecting the concentrate and permeate streams to a series of evaporation and ion exchange processes to recover distillers dried grain and solubles and glycerol, succinic and lactic acid. Kampen does not recover solids for methane gas production and rejects water as evaporate rather than recovering it.

Still bottoms can contain a wide range of insoluble and soluble solids in particulate and dissolved state that require removal before a pure potable water can be produced. Evaporation can separate non-volatile and suspended solids from a liquid condensate and centrifugation can separate suspended solids to approximately 1 micron from a liquid stream. Microfiltration can further separate coarse particles to between 10 and 0.1 microns, ultrafiltration finer particles and colloids sized to between 0.1 to 0.005 microns, nanofiltration particles and high molecular weight molecules to between 0.005 and 0.001 microns, and reverse osmosis particles and molecules to 0.00005 microns. Generally, microfiltration has a molecular weight cutoff of 0.1 million Daltons, ultrafiltration a molecular weight cutoff of 10,000 Daltons, nanofiltration 700 Daltons and reverse osmosis a molecular weight cutoff of 50-100 Daltons. Pressurized membrane assemblies can be tubular, hollow-fiber, spiral-wound, or flat plate with inlet pressures 40 bars or greater most often used. Spiral wound cross-flow filters are most efficient. Membranes for use at high temperatures are manufactured of the polyamide type.

As disclosed in the treatment of a sugar and starch wastewater, U.S. Pat. No. 6,036,854 to J. Potter, a concentration process using ultrafiltration is positioned at the front of a treatment system to convey the concentrates to a mixing tank for hydrolyzing the starch to sugars and adding nutrients to form a feedstock to a fermentation tank that grows yeast cells. However, the permeate from the ultrafiltration is discharged to the sewer and is not beneficially used.

As disclosed in U.S. Pat. No. 6,423,236 to Shiota, et al., a reverse osmosis system is used following wet-oxidation of organic wastewaters at high temperatures to separate molecules into the concentrate stream with acetic acid salts preferentially being the molecular weight of the concentrate cut off produced in the energy intensive wet oxidation process. In the preferred embodiment, Shiota, et al., suggest food processing wastes among many others as one possible organic source, option for elimination of wet-oxidation, and a non-descriptive anaerobic fermentation of the concentrate and household water use of the permeate from the reverse osmosis system. However, Shiota et al., make no specific claims to anaerobic fermentation or type in their invention, use of any methane gas to power the pressurized filtration system, recovering ammonia from the anaerobic fermentation to adjust pH before reverse osmosis, claim a temperature of 40 Celsius or below in reverse osmosis and a minimum concentration of 30 weight percent of an oxidizable substance as feedstock. For pasteurization to be in effect (70 Celsius for 30 minutes) would require a hot wet oxidation pre-treatment of this concentrated waste using the Shiota et al process before separation by reverse osmosis. Shiota, et al., therefore do not address the combined conditions necessary to separate fermentation still bottoms or many other similar food processing wastes by ultrafiltration or reverse osmosis before anaerobic digestion and to treat the concentrate by anaerobic digestion to recover energy to produce potable water for human consumption. The Shiota et al., process is disadvantageous to still bottom discharges because its descriptive specifications of concentration and temperature thresholds do not match those of fermentation still discharges or specific anaerobic fermentation processes and it would not be cost effective to adjust those parameters by further concentration, dilution and cooling not specified or disclosed.

Conventioanl anaerobic fermentation to produce methane gas is a mixed culture microbial process of liquefaction, acidogenisis and methanogenisis. Shiota et al., is using an energy intensive physical chemical process of wet-oxidation of organic wastewaters followed by reverse osmosis and is not descriptive of and is deficient in the specifications for a pressurized filtration system before anaerobic digestion to separate solids and liquids in an energy efficient and sanitary process without wet-oxidation.

Methanogenic bacteria are strictly anaerobic and die in the presence of oxygen. Unlike aerobic bacteria that convert its feedstock into microbial biomass and carbon dioxide through oxygen respiration, anaerobic bacteria convert its feedstock primarily into methane gas by a metabolic transfer of hydrogen. Methanogenisis is descriptive of an efficient biofuel cell process. Conventional anaerobic fermentation of concentrated organic wastes, particularly fermentation distillery discharges, use a variety of methods to increase the rate of degradation in order to decrease the size of the reactor and improve efficiency. Liquefaction (hydrolysis) and methanogenisis are rate limiting when performed together and hydraulic retention times toward 20 days and loading rates much less than 10 kg COD/cubic meter-day are often required for the mixed bacterial cultures to work efficiently together. Because the methanogenic bacteria are slow in reproductive growth rates and are sensitive to pH, they are most often rate limiting in the presence of an excess of fermentable acids, such as acetic and proprionic acids. For example, if hydrolysis occurs more rapidly than the slower methanogenisis, a build up of acidic conditions can occur and destroy the methanogenic bacteria. On the other hand, if the waste contain recalcitrant organics, hydrolysis will occur slowly limiting the feedstock for the methanogenic process. Various process control factors are used to improve efficiency of methanogenisis, including increasing mean cell residence times, separating hydrolysis and acidification from methanogenisis and increasing reaction rates by increasing temperatures that in turn culture a different and more efficient mixed bacterial culture.

Anaerobic lagoons, continuously stirred tank reactors (CSTR), CSTR's operated in contact mode, anaerobic filters, upflow anaerobic sludge blanket reactors (UASB), anaerobic fluidized bed reactors, and expanded bed reactors are among the technologies used for the distillery industry. The UASB reactor enhances reaction rate by increasing mean cell residence times by recirculating within the reactor granular particles and bacterial flocs that float on the surface that separates the reaction locations of acidification (5 days) and methanogenisis (7 days) in the reactor (see U.S. Pat. No. 5,773,526, Van Dijk, et al). The UASB method is sometimes dependent on preventing interfering flocs and too high of a strength of organic and suspended solids can inhibit reactions, often times requiring dilution. Though studied to operate in thermophilic mode (50-65 Celsius), reaction rates tend to be greater and interfere with floc formation. UASB systems are frequently used on distillery wastewaters and research has shown loading rates when operating in thermophilic mode of 16 kg of COD per cubic meter-day with 90% destruction for cane sugar distillery discharges. UASB systems can not operate at high suspended solids loadings.

CSTR reactors are conventional anaerobic digesters for high suspended solids loading and the hydraulic and mean cell residence times are about the same. The mean residence time of cells can be increased by separating cells from discharge and recirculating in contact mode. Studies of high concentration agricultural wastes operating in thermophilic contact mode at 8 day retentions have shown loading rates of 9 kg COD/cubic meter-day with 75% destruction and improved performance in thermophilic over mesophilic in destroying COD and enhancing the rate of liquefaction and methanogenisis. Compared to a CSTR system that doubles the solids concentration before anaerobic digestion, the UASB system exposes over 50% more water to bacterial degradation and consequently discharges a greater volume from the digester for waste management.

Pressurized membrane systems are used to refine and produce drinking water from wastewater. In U.S. Pat. No. 6,368,849, Norddahl invents a CSTR anaerobic fermentation process that recovers energy to power an ultrafiltration and denitrification device. Norddahl's ultrafiltration device is placed after anaerobic bacteria consume organic wastes. This process is disadvantageous if applied to fermentation still bottoms for beneficial drinking water recovery because there would be no separation of the beneficial characteristics of the pasteurized still bottoms into the permeate before bacterial degradation and contact. Nitrogen is recovered as aqueous ammonia for use as a fertilizer. In U.S. Pat. No. 5,374,356 Miller et al invent a ultrafiltration and nanofiltration device for treating wastewaters, particularly gray water, in closed environments such as ships for conserving and recycling the permeate as potable water. The invention is disadvantageous as it means not to produce methane through anaerobic fermentation of the concentrate for an energy efficient pressurized filtration and means not to produce a potable water under sanitary conditions from pasteurized feedstock for human consumption.

There are many beneficial properties to fermentation still bottoms including industrial, medicinal, nutritional, or commercial chemical product uses including when reprocessed further to simple chemical monomers. For example, a combination of cellulase and xylanase enzyme preparations to distillers dried grains solubles (DDGS) releases 96% of the glucose, 50% of the xylose, and 54% of the arabinose in DDGS carbohydrates (DOE Grant #DE-FG36-04GO14220, 1999). Though reports show means to enzymatically convert these carbohydrates to sugars, they do not show an industrial application to produce the carbohydrates and recover these sugars as this invention embodies. The sugars below 700

Dalton in molecular weight can be separated by membrane technology into a permeate, with the higher molecular weight residuals subjected to anaerobic digestion. Medicinal properties of fermentation include resveratrol, a well known antioxidant found in grapes and other plants. Resveratrol is found to be released from grapes by fermentation into wine and to be a cancer chemopreventative agent in mammals, including humans. In U.S. Pat. No. 6,861,085 Melwitz et al, describe a process for preparing a concentrate containing red wine extract and in U.S. Pat. No. 6,008,260 Pezzuto et al describe a solvent extraction procedure for isolating resveratrol. In the distillation of wine to make brandy, resveratrol with a molecular weight of 230 Dalton, would be present in the still bottoms and the concentrate fraction of reverse osmosis together with other minerals, nutrients and chemicals. There are no known processes that isolate and concentrate resveratrol from brandy stillage nor are there beverages derived from fermentation still bottoms that deliver these beneficial properties to a consumer.

Fermentation still bottoms can occur after a first membrane separation of solids and then a removal of ethanol from the liquid stream. For example, in U.S. Pat. No. 4,999,209 Gnekow removes volatile substances including alcohol from wine through a double reverse osmosis process and Weiss in U.S. Pat. No. 4,812,232 separately removes wine solids by reverse osmosis and then ethanol by vacuum distillation. In U.S. Pat. No. 4,988,525, Gresch uses a a diaphragm solids separation device followed by column distillation of ethanol. The objective is to make a non-alcoholic wine by recombining the wine concentrates with the liquid after the alcohol removed or separate the volatile acids from the alcohol before adding purified alcohol back to wine concentrate with makeup water. Potable water from fermentation still bottoms by solids removal is not the objective of these applications where solid removal is to concentrate wine solids first before the removal of ethanol from the volatile organic liquid stream.

Pressurized membrane systems are used to manufacture a water of beneficial character for commercial retail sales. The bottled water retail market is over $45 billion. There is a consumer demand for bottled water as a beverage because the source, process and composition is known and reliable and specific sealed and labeled sources containing nutrients or nutritious sources are more valuable to a health conscious consumer than bottled water from a generic source. Bottled water is frequently marketed and labeled as reverse osmosis or ultrafiltered water to gain acceptance that it has been treated and additives are often introduced to enhance nutritional value, color, odor and taste. With groundwater contamination, air pollution fallout and runoff into water bodies, spring water and river waters are becoming less reliable sources. There is a limited product on the market where bottled water is obtained directly from the feedstock of a pasteurized source and there are limited, if any, beverages known on the market derived directly from the filtration of fermentation still bottoms, or that also contain the natural nutrients and medicinals of fermentation still bottoms.

OBJECTS AND ADVANTAGES

The objectives and advantages of our invention as discussed above in relation to the disadvantages of the prior art are numerous and several of the objects and advantages of the present invention are:

(a) to provide a unique process that separates under sanitary conditions the solid and liquid components of a nutrient rich pasteurized stream of fermentation still bottoms and converts the solid organic concentrate to methane fuels and collects the permeate as a nutrient rich or clean and clear fraction for human consumption as a beneficial water;

(b) to provide a pressurized filtration that maintains the pasteurized character of discharged still bottoms in a sanitary state to produce a beverage aseptically before any other process that might be septic;

(c) to provide a beneficial liquid product of fermentation residues at predetermined molecular weight cutoffs providing a superior water product that is reliable, safe and appealing for human consumption with or without further refinement and additives;

(d) to provide a clean permeate water to be recycled into the pre-distillation fermentation process, as boiler makeup water, or discharged in volume and concentration as permitted acceptably into the environment;

(e) to provide filtration before anaerobic digestion to lessen the hydraulic load on a CSTR reactor and thus reduce the hydraulic volume of wastewater discharged from the CSTR reactor for subsequent waste management;

(f) to provide a method to produce a liquid ammonia solution from the anaerobic digestion process to recover as a fertilizer, to provide a nitrogen source to culture yeast before ethanol fermentation or used with other alkali to adjust pH of nanofiltration permeates, to form ammonium salts, and other ammonia based products.

(g) to provide a process to pressure filter before anaerobic digestion to produce a less solids concentrated and diluted permeate stream allowing such stream to be treated by a UASB or similar anaerobic process to produce fuel value methane gas;

(h) to provide a process to pressure filter before anaerobic digestion to increase the solids concentration to more optimal conditions for a CSTR reactor;

(i) to provide a total process operated above 50 C that conserves the heat entropy of the discharge to operate pressure filtration in a pasteurized state and CSTR anaerobic fermentation at thermophilic temperatures;

(j) to provide a in line process to pressure filter before anaerobic digestion to recover sanitary pasteurized beneficial water and returning separated solids to be diluted with makeup water for treatment by a UASB or similar fermentation process to produce fuel value methane gas;

(k) to provide a process to filter before anaerobic digestion with means for converting the concentrated solid organics to produce methane gas of a fuel value to power the pressurized filtration system and other energy systems within and outside the process;

(l) to provide a process to reduce the volume of the reactor by operating in a thermophilic temperature range that increases degradation rates and also advantageously settles or separates the solids from the anaerobic discharge to allow 1) efficient return of active cells to the anaerobic fermentation process to increase mean cell residence time and further increase degradation rates and, 2) to collect said anaerobic discharge solids to apply to land as a nutrient compost (m) to recover nutrient broths including resveratrol from separated low molecular weight fractions of solids and to recover fermentable sugars for increased ethanol efficiency by enzymatic processing of unfermented carbohydrates and other chemicals.

In addition, further objects and advantages among many others are to provide a process which produces a safe and reliable higher value added water product for human consumption making the process more economical and advantageous as an asset compared to wastewater treatment of fermentation still bottoms per se' that are generally looked upon as a financial liability to the generator who is unable to otherwise quantify the economic value of the treatment process.

SUMMARY OF THE INVENTION

In accordance with the present invention a method is provided to make clean water and a non-alcoholic beverage directly from fermentable still bottoms through a solids separation and pressurized filtration process that also concentrates solids for anaerobic digestion to recover methane fuels and to recover useful by-products before anaerobic fermentation. This process comprises first removing solids from the liquids of still bottoms that are discharged pasteurized by one or more of the steps within solid-liquid removal groups to produce a potable water and conveying the separated solids to anaerobic fermentation after beneficial properties have been recovered. The anaerobic fermentation discharge can be separated advantageously under thermophilic conditions with solids optionally returned to the process to increase mean cell residence time and the liquid stream denitrified to produce ammonia to recycle. Though unit processes can be operated separately, when operated in proximity and at thermophilic temperature (50 C-65 C) obviates the need for cooling when filtered at temperatures of pasteurization, and retains beneficial properties to both the permeate purification and anaerobic digestion process.

BRIEF DESCRIPTION OF THE DRAWING

Drawing 1 is a conceptual diagram of the method for treating still bottoms in the embodiment of the present invention.

Drawing 2 is a schematic diagram of the method for treating still bottoms in the embodiment of the present invention.

Drawing 3 is a schematic of by-product recovery from separated solids before anaerobic femerntation in the embodiment of the present invention.

DETAILED DESCRIPTION—DRAWING 1,2 AND 3—PREFERRED EMBODIMENTS

Referring now to the drawings there is shown a conceptual diagram of the preferred embodiment of the process and system Drawing 1 for still bottom treatment to recover fuel and beneficial water in accordance with the present invention and a specific schematic diagram Drawing 2 of the method. Drawing 3 illustrates methods to process and recover beneficial by-products from the solid stream.

As shown a discharge stream 2 of still bottom issues from an alcohol distillation facility at temperatures greater than 70 C and less than 100 C constituting a pasteurized state. The stillage can be conveyed through appropriate piping or transported and though not necessarily captured within this temperature range, the still bottoms should be maintained sanitary and preserve the characteristics of the spent yeast cells and cell parts, metabolites, fermentation byproducts, and non-fermentable starch and sugar feedstock residues without biological degradation or microbial contamination. Starch and sugar feed stocks can consist of any type of fermentable carbohydrate in the presence of an ethanol producing microbial strain. These starch and sugar feedstocks can include molasses, cane sugar, corn starch, barley, other grains such as rice, and fruits such as grapes and grape skins, and cellulose broken down to sugars through physical chemical and enzymatic processes, and starch converted to sugars with amylase. Other hot organic materials that are not from still bottoms but meet these characteristics, such as discharges from high temperature processing of food products, or wine before distillation can also be a feedstock. The preferred non-ethanol solids concentration of spent yeast cells and cell parts, metabolites, fermentation byproducts, and non-fermentable starch and sugar feedstock residues in the still bottom discharge may be a total solids concentration less than 10% w/w in water, more typically from 1% to 7%, with a COD concentration from 20,000 to 80,000 ppm. The specific rate of discharge will depend on the nature of the primary processing facility, but is typically on the order of at least 10,000 up to 250,000 gallons per day or greater and at a temperature above 70 C but can be less.

There is a wide variation in the composition and content of solids in fermentation still bottom liquid stream 2 issuing from the distillation processes. Some still bottoms such as corn mash require removal of coarse solids 20 and fine solids 10 before potable water can be produced, and others such as following wine distillation in pot stills to make brandy or when solids of wine are removed before distillation, virtually minimal if any solid removals before completion steps of pH adjustment 65, reverse osmosis 16, and finishing 26a to render a potable bottled water product 26. The quality of the composition and the content of solids in the still bottom liquid determines the amount of coarse, fine and molecular levels of solids removal by centrifugation or evaporation 20 and pressurized membrane filtrations 10 to achieve a desired quality of liquid input to the completion steps and as appreciated by those skilled in the art all, several or no stages of solids removal can be predetermined according to the initial characteristics of the still bottoms.

In the preferred embodiment, the pasteurized still bottom stream 2 first flows through a two-way valve 4 to stream 6 where it is pressurized 8 to between 15 and 40 bar and enters a membrane filtration system assembly 10. Although the present embodiment illustrates a single membrane 10, any number and types of membranes may be required to achieve sufficient liquid quality devoid of solids. Comprising one or more of the group of microfiltration to 0.1 micron, ultrafiltration to 0.001 micron and nanofiltration with a molecular weight cutoff of 700 Daltons, a predetermined low solid liquid issues 11. The concentrate 28 is conveyed to line 30 through appropriate piping or transported. The pasteurized stream in its preferred embodiment is first filtered at an inlet temperature between 70-80 C although filtration can occur between 25-70 C when cooled and sanitary conditions are maintained. There is an inverse relationship between the size of the pores to prevent still bottom solids from passing through and fouling the membrane, and the pressure required to force water and smaller solids through. The frequency of cleaning required (CIP) and stages of filtration depend upon the size, concentration and composition of the solids in the still bottom 2 in respect to the low solid liquid that issues 11. Cross-flow pressurized filtrations in spiral wound membranes are preferred to minimize fouling and frequency of cleaning. In a rare circumstance there can be still bottoms 2 equivalent to the desired low solid liquid 11 and do not require aggressive solids removal.

When the discharge is a "heavy stillage" that can foul pressurized membrane filtration or has a coarse suspended solid that has other by-product value such as distillers dried grain, the heavy stillage is directed by the two-way valve 4 to a centrifugal decanter 20 or other coarse solid-liquid separating device such as microfiltration or evaporation and separated into thick 22 and thin 24 fractions with a predetermined amount of the thick fraction to be recovered as a by-product by line 22a such as distillers dried grain and through line 23 by-passing pressurized filtration to enter line 30. The thin fraction or as in the case of evaporation the condensate in line 24 returns to the main stream 6 before pressurized filtration less a predetermined fraction that is between 0.0 and 0.9 directed by line 25 to line 30.

Now returning to the pressurized filtration assembly 10, they are a plurality of spiral wound membrane filters although other membrane filters such as flat plate, tubular and hollow-fiber can be used, and in its preferred embodiment is cross-flow filteration. With pasteurized inlet temperature >70 C the filter is of a polyamide type. In the absence of coarse solids removal or where solids can foul ultrafiltration and nanofiltration, a microfiltration first occurs to a predetermined level between 10 and 0.1 micron. The permeate continues pressurized into one or sequentially both an ultrafiltration of fine particles to a cutoff of 0.01 microns (10,000 Daltons) and a nanofiltration of high molecular weight insoluble and dissolved solids that has a predetermined molecular weight cut-off of approximately 0.0007 microns (700 Dalton) so that the liquid issuing 11 generally has solids as colloids and molecules from the still bottoms that are below this predetermined size. The liquid issuing 11 and withdrawn 12 from the process in whole or in part is discharged to the environment, is treated by aerobic or anaerobic processes (see U.S. Pat. No. 5,773,526 for example), or recovered for beneficial properties such as into 27a Drawing 3 (see U.S. Pat. No. 6,861,085 for preparing a concentrate containing red wine extract and U.S. Pat. No. 6,008,260 a solvent extraction procedure for isolating resveratrol).

The liquid remaining 11, or when the still bottoms are very thin to start and would otherwise have the solid concentration and characteristics of the desired liquid including from any one or more of the solid removal techniques, such as the still bottom from a prefiltered distilled wine, the distillation in a brandy pot still, or the condensate from evaporation, line 11 is then neutralized to a predetermined pH level between 4 and 7.5 by addition of an alkali for pH adjustment line 65, repressurized 14 to 20-50 bar to flow into the reverse osmosis (RO) filtration assembly 16 where the concentrate with a molecular weight greater than 50-100 Daltons is passed to line 28 and the reverse osmosis permeate is passed to finishing steps 26a.

As illustrated in Drawing 3, line 27 withdraws and conveys the RO concentrate to recover any beneficial properties of the fraction greater than 50 to 100 Daltons before anaerobic digestion. In its preferred embodiment the recovery of beneficial properties can include the further concentration by evaporation 27a to make a nutrient broth 27c as described in U.S. Pat. No. 6,861,085 and should resveratrol be desired to be extracted from 27c a recovery performed as described in U.S. Pat. No. 6,008,260 including with solvent extraction. These recovery processes can be performed remotely by the bulk transport of RO concentrate line 27. The condensate 27b with volatile organics is returned to line 28 to anaerobic digestion that can also be a upflow anaerobic sludge blanket reactor (UASB).

In the preferred embodiment, the RO assembly 16 have cross-flow spiral wound membrane filters although other membrane filters can be used. When inlet temperature >70 C the filter is of a polyamide type. The RO permeate 26 is clear clean water with low levels of small molecular weight organics and this RO permeate passes through one or more of a group of predetermined finishing steps 26a including a) heat exchanger to cool to 25-30 C, b) activated carbon or ion exchange, c) aeration, d) vacuum distillation or degasification, e) adjustment of pH to a neutral level, and f) addition of nutrients. From 50-70% of the inlet volume to the pressurized filtration assembly is converted to a beneficial distillers water in this process, the product a highly marketable grade drinking water for bulk handling or bottling.

The combined concentrate from solids removal and pressurized filtration in line 28 is 2-5 times the initial concentration of total solids (TS) in the still bottoms but should be limited to a predetermined maximum level to no more than 10-25% TS in line 30. If TS is less than 5% it can be treated in a UASB or equivalent anaerobic digester. In its preferred embodiment the concentrate in line 30 is at a temperature between 50-65 C but can be from 25-50 C Line 28 can be a bulk transfer to a remote digester system and enters line 30 that enters an anaerobic fermentation tank 32 and in its preferred embodiment is a completely stirred tank reactor (CSTR) operating within thermophilic temperature range of 50-65 C, although it can be operated in a mesophilic temperature range of 30-50 C and with low concentration of solids to a UASB anaerobic system. To maintain TS concentration at a maximum predetermined level no more than 10-25% TS, line 30 can also receive thick 23 and thin 25 stillage, recycled water and bacterial cells from the anaerobic fermentation discharge 48, and makeup water from an outside source 64. To also maintain the concentration in line 30 at the maximum predetermined acceptable level no more than 10-25% TS, the concentrated permeate is additionally withdrawn from line 29 to reduce the line 30 concentration. This withdrawn concentrate is for use other than fuel production in anaerobic fermentation (see U.S. Pat. No. 6,036,854 for example), and can be blended with line 22a to supplement distillers dried grain (see U.S. Pat. No. 5,250,182 for example), reprocessed to produce more sugars for ethanol fermentation, or for other uses such as industrial, medicinal, nutritional, or commercial chemical products as described for line 29 below.

In its preferred embodiment when producing distillers dried grain solubles (DDGS) from pressurized membrane filtration of stillage or other concentrates such as residuals from cellulosic sugar fermentations, line 29 conveys the separated solids to byproduct reprocessing to make simple monomers or chemical precursors. For example and as illustrated in Drawing 3 from a published DDGS reprocessing method, the concentrate 29 is passed to a retort vessel 29a to pretreat the concentrate at 15% solids at 160° C. for 20 min and commercial enzymes including predetermined concentrations of GC 220+Novo 188+binary combination of xylanase and hemicellulase are added and reacted at 50° C. & pH 4.8 (citric acid buffer) for 72 hrs to produce up to 30% fermentable sugars from the non fermentable DDGS carbohydrates. The resulting product solution is composed of fermentable sugars and can be pressure filtered through predetermined sized polyamide membranes 29b with the permeate 29d composed of fermentable sugars and the concentrate of residual DDGS conveyed by line 29c into line 30 and the CSTR reator 32. 29d can be a remote transport to fermentation. Other processing such as from the stillage concentrate of lignocellulose conversions to sugars for ethanol fermentations can yield a variety of useful byproducts through biological, chemical and physical methods.

In the preferred embodiment the loading rate to a CSTR anaerobic digester is at a predetermined level between 5-10 kilograms COD per cubic meter per day (kg/m3-d) and the reactor adjusted in volume and number of reactors to accommodate the influent COD level, with a minimum of two reactors operated in parallel. The reactor should be optimally designed at a predetermined hydraulic retention time between 15-25 days however adjustments can be made to allow for toxic interferences such as ammonia and sulfides. The CSTR process is a conventional anaerobic fermentation method and continuously stirs the concentrate. Methanogenic bacteria generating methane gas and other gases such as carbon dioxide and hydrogen sulfide are exhausted from the reactor 34 where the hydrogen sulfide is removed by conventional desulphurization processes with the resulting fuel gas of moderate energy value of 600-750 btu/ft3. The carbon dioxide is optional for removal for commercial use or fixed from entering the atmosphere but in the preferred embodiment the methane with carbon dioxide is converted to electricity 36 in a gas turbine or by other means with the electricity used to power the pressurized filtration process and the net electricity balance used to power auxiliary systems 37 within the process, in the fermentation distillery plant, or transferred to a utility supply grid. The fuel gas can also be conveyed 35 to another energy conversion process, such as boiler fuel, and the pressurized filtration process operated independent of fuel gas production by use of an outside fuel source or electricity supply 38.

The liquid discharge from the CSTR anaerobic fermentation 40 is conveyed to a centrifugal decanter 42 where it is separated into a solid stream 44 and liquid stream 52. The solid stream contains the majority of bacterial cells and non degraded suspended solids and a predetermined amount is divided by a two-way valve 46 into a return line 48 to the CSTR fermenter and the remaining 50 to a landfill as a compost. The liquid stream from the centrifugal decanter can be disposed of directly or denitrified (see U.S. Pat. No. 6,368,849) but in the preferred embodiment it is first pressure filtered by nanofiltration 54 where the concentrate 56 is a thick fluid and disposed in a sewer or hauled to a sewage treatment plant. The permeate stream 58 is primarily dissolved inorganic and organic solids including ammonia and undergoes denitrification 59 and recovery consisting of a) aqueous ammonia solution as fertilizer 63 or for other ammonia based chemicals, b) return to the process as nutrient for yeast culturing and as an alkali to adjust the pH of the permeate input to reverse osmosis by line 61. An alkali other than aqueous ammonia solution can be supplied to adjust the pH of the permeate input to reverse osmosis by line 65. Following denitrification, a predetermined amount of the permeate stream is divided by a two-way valve 60 into the return line 48 as makeup water to the CSTR fermenter and the remaining 62 to an outside receiver.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which fall within the purview of the subject invention.

We claim:

1. Means for separating a coarse solid from a liquid portion in a soluble and insoluble organic and inorganic ethanol fermentation still bottom discharge by pressurized microfiltration of the coarse solid from the liquid portion of the soluble and insoluble organic and inorganic ethanol fermentation still bottom discharge and separately conveying each said coarse solid and liquid portion at predetermined volumes to a concentrate line for anaerobic digestion and remainder of said liquid portion to a pressure filtration line to further separate solids and liquids to render a potable water product.

2. A potable water product from ethanol fermentation still bottoms through a process to separate pasteurized still bottom liquid from solid organic and inorganic components by continuously subjecting the still bottom liquid to steps that further separate the organic and inorganic concentrate fractions of solids of lesser weight from the still bottom liquid, whereby the separated solid concentrate fractions are anaerobically digested after beneficial properties recovered, with a sequence of steps to obtain first a predetermined composition and solids content in a rendered liquid consisting essentially of a first step of coarse solids separation by centrifugation or evaporation or microfiltration followed by a pressurized membrane filtration step to further separate solids as selected from the group consisting of microfiltration and ultrafiltration and nanofiltration, with the rendered liquid having the predetermined composition and solids content, followed by an adjustment of pH step of the rendered liquid to a predetermined level of pH, followed by a pressurized reverse osmosis step through a semi-permeable membrane of a molecular weight pore size between 50-100 Dalton producing a reverse osmosis concentrate and a reverse osmosis permeate, followed by a finishing step to the permeate, to yield the potable water product of low molecular weight solids of still bottoms used for recycling, discharge, or human consumption by bulk handling or bottling.

3. The process in claim 2 wherein solid removal by microfiltration, ultrafiltration and nanofiltration have, respectively, a solids size cutoff of 0.1 micron or 0.1 million Dalton, 0.01 micron or 10,000 Dalton, and 0.0007 micron or 700 Dalton.

4. The process in claim 2 wherein the still bottoms are pasteurized and pressure filtered by semi-permeable membrane filters at inlet pressures of 20-50 bar in cross-flow spiral-wound filtration assemblies at temperatures between 25-80 C and are of a polyamide type when temperatures of filtration are greater than 65 C.

5. The process in claim 2 wherein the rendered liquid is adjusted with an alkali to neutralize organic acids at a predetermined pH between 4.0 and 7.5 before pressurized reverse osmosis.

6. The process in claim 2 wherein the rendered liquid is anaerobically treated in an upflow anaerobic sludge blanket reactor and the separated solid concentrate used to recover beneficial properties and the resulting solids and liquids returned to anaerobic digestion or the process in claim 2.

7. The process in claim 2 wherein the separated solid concentrate is heated in a vessel at 15% concentration up to 0.5 hr at 160° C. and issued to a second vessel at 50° C. and pH 4.8 for 72 hours wherein commercial carbohydrate degrading enzymes of predetermined type and concentration are added and the reactant is pressure filtered with a permeate that can be refermented to yield ethanol and a concentrate sent to anaerobic digestion.

8. The process in claim 2 wherein the reverse osmosis concentrate is evaporated with the condensate returned to anaerobic digestion and beneficial properties of a more concentrated solution recovered including by solvent extraction of resveratrol and aliquots of the concentrated solution added as the nutrient broth to the water product as part of the finishing to the reverse osmosis permeate.

9. The process in claim 2 wherein the reverse osmosis permeate is finished before bulk handling or bottling including with the following a) heat exchanger to cool to 25-30 C, b) activated carbon or ion exchange, c) aeration, d) vacuum distillation or degasification, e) adjustment to a neutral pH, f) augmentation with beneficial properties.

10. The process of claim 2 wherein the reverse osmosis permeate or finished product is reused or discharged.

11. The process of claim 2 wherein the separated solid concentrate fractions are transported in pipe or bulk for remote anaerobic digestion following a remote beneficial property recovery and the rendered liquid, reverse osmosis permeate and the potable water product transported in pipe or bulk for remote finishing, bottling or for direct human consumption.

12. The organic and inorganic concentrate fractions of claim 2 wherein beneficial properties of concentrates are recovered before anaerobic digestion and the separated non-beneficial concentrate returned to anaerobic digestion, beneficial properties of the fractions including distillers dried grain, distillers dried grain solubles, medicinals, chemicals, including reprocessing concentrate to make sugars, ethanol, simple monomers and nutrients including the nutrient or medicinal return to the potable water.

13. The organic and inorganic concentrate fractions of claim 2 wherein total or separate fractions of solid organic concentrate is anaerobically digested including under thermophilic conditions to liquefy insoluble organics to improve acidogenisis, hydrogen production efficiency and methanogenisis.

14. The anaerobic digestion of claim 2 wherein a gas of methane fuel value is produced and used to recover its energy value and methane is separated from carbon dioxide gas of no fuel value and the enriched gas separately used for its energy value and the carbon dioxide recovered for useful purposes or fixed from entering the atmosphere.

15. The organic and inorganic concentrate fractions of claim 2 wherein the total or separate fractions of organic solids is anaerobically digested to produce by a predetermined process a ammonia solution for use as a fertilizer, for recycling to the ethanol fermentation process as a nutrient for yeast culturing, as a buffering agent to neutralize acids, and for production of ammonia based products.

16. The organic and inorganic concentrate fractions of claim 2 wherein clean water is separated from the concentrate following anaerobic digestion by a sequence of steps that continuously subjects the concentrate to steps that further separate fractions of solids of lesser molecular weight from the concentrate, the steps consisting of anaerobic digestion, centrifugation, and ultrafiltration-nanofiltration through a semi-permeable membrane with a molecular weight pore size no less than 700 Dalton, recovery of ammonia by a predetermined process from the permeate, the resulting product being clean water for reclamation, discharge, or reuse.

17. The process in claim 2 whereby the still bottoms, without any of the steps comprising the coarse solids separation and the pressurized membrane filtration to further separate solids, have the predetermined composition and solids content of the rendered liquid, are treated as the rendered liquid and continued to completion steps of adjustment of pH of the rendered liquid to a predetermined level of pH, pressurized reverse osmosis through a semi-permeable membrane of a molecular weight pore size between 50-100 Dalton producing a reverse osmosis concentrate fraction anaerobically digested after beneficial properties recovered and a clear potable liquid reverse osmosis permeate that is finished to render the potable water product of low molecular weight solids of still bottoms used for recycling, discharge, or human consumption by bulk handling or bottling.

18. A potable water product from ethanol fermentation still bottoms through a process to separate pasteurized still bottom liquid from solid organic and inorganic components by continuously subjecting the still bottom liquid to steps that further separate the organic and inorganic concentrate fractions of solids of lesser weight from the still bottom liquid, whereby the separated solid concentrate fractions are anaerobically digested after beneficial properties recovered, with a sequence of steps first step to produce a predetermined composition and solids content in a rendered liquid selected from the group consisting of solids separation by centrifugation and evaporation and microfiltration and ultrafiltration and nanofiltration and reverse osmosis issuing said rendered liquid, followed by an adjustment of pH step of the rendered liquid to a predetermined level of pH, followed by a pressurized reverse osmosis step through a semi-permeable membrane of a molecular weight pore size between 50-100 Dalton producing a reverse osmosis concentrate and a reverse osmosis permeate, followed by a finishing step to the reverse osmosis permeate to yield the potable water product of low molecular weight solids of still bottoms used for recycling, discharge, or human consumption by bulk transport or bottling.

19. The process in claim 2 whereby the still bottoms, without the first step to produce a predetermined composition and solids content in a rendered liquid by solids separation, are treated as the rendered liquid and continued to completion steps of adjustment of pH of the rendered liquid to a predetermined level of pH, pressurized reverse osmosis through a semi-permeable membrane of a molecular weight pore size between 50-100 Dalton producing a reverse osmosis concentrate fraction anaerobically digested after beneficial properties recovered and a clear potable liquid reverse osmosis permeate that is finished to render the potable water product of low molecular weight solids of still bottoms used for recycling, discharge, or human consumption by bulk handling or bottling.

20. A potable water product from ethanol fermentation still bottoms through a process to separate pasteurized still bottom liquid from solid organic and inorganic components by continuously subjecting the still bottom liquid to steps that further separate the organic and inorganic concentrate fractions of solids of lesser weight from the still bottom liquid with a sequence of steps to produce a predetermined composition and solids content in a rendered liquid selected from the group consisting of solids separation by centrifugation and evaporation and microfiltration and ultrafiltration and nanofiltration and reverse osmosis issuing said rendered liquid, an adjustment of pH step of the rendered liquid to a predetermined level of pH, a pressurized reverse osmosis step through a semi-permeable membrane of a molecular weight pore size between 50-100 Dalton producing a reverse osmosis concentrate and a reverse osmosis permeate, and a finishing step to the reverse osmosis permeate to yield the potable water product of low molecular weight solids of still bottoms used for recycling, discharge, or human consumption by bulk transport or bottling.

* * * * *